US00PP13249P3

(12) United States Plant Patent
Utecht

(10) Patent No.: US PP13,249 P3
(45) Date of Patent: Nov. 19, 2002

(54) GERANIUM PLANT NAMED 'FISROBRAV'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/991,785

(22) Filed: Nov. 26, 2001

(65) Prior Publication Data

US 2002/0088039 P1 Jul. 4, 2002

(51) Int. Cl.[7] ..... A01H 5/00

(52) U.S. Cl. ..... Plt./325

(58) Field of Search ..... Plt./329, 325

*Primary Examiner*—Kent L. Bell
(74) *Attorney, Agent, or Firm*—Foley & Lardner

(57) ABSTRACT

A new and distinct cultivar of geranium plant named 'Fisrobrav', as described and illustrated, and particularly characterized by the combined features of bluish-pink round flowers with cherry-red eyes, medium sized umbels well above the foliage, medium green foliage with weak zonation, and moderately vigorous growth.

1 Drawing Sheet

BOTANICAL CLASSIFICATION

*Pelargonium zonale.*

VARIETY DENOMINATION

'Fisrobrav'.

BACKGROUND OF THE INVENTION

The present invention comprises a new and distinct cultivar of geranium, botanically known as *Pelargonium zonale*, and hereinafter referred to by the cultivar name 'Fisrobrav'.

'Fisrobrav' is a product of a planned breeding program which had the objective of creating new geranium varieties with pink to purple-pink flowers with eyes in combination with medium green foliage and medium to tall plant habit.

'Fisrobrav' originated from a hybridization made by the inventor Angelika Utecht in a controlled breeding program in Galdar, Gran Canaria, Spain, in 1996. The female parent was the patented cultivar 'Fisbravo' (U.S. Plant Pat. No. 9,765), which is characterized by pink colored flowers with large purple eyes, dark-green, slightly zoned foliage and moderately compact plant habit. The male parent of 'Fisrobrav' was the commercial cultivar 'Valentine' (U.S. Plant Pat. No. 10,587), having violet-pink, semi-double flowers with white eyes, dark green foliage without or with only very slight zonation, and moderately compact plant habit.

'Fisrobrav' was selected as one flowering plant within the progeny of the stated cross by Angelika Utecht in 1997 in a controlled environment in Galdar, Gran Canaria, Spain. The first act of asexual reproduction of 'Fisrobrav' was accomplished when vegetative cuttings were taken from the initial selection in the fall of 1997, in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fisrobrav' are firmly fixed and are retained through successive generations of asexual reproduction. The new cultivar reproduces true to type.

'Fisrobrav' has not been observed under all possible environmental conditions. The phenotype may vary significantly with variations in environment such as temperature, light intensity and day length.

The following observations, measurements, and comparisons describe plants grown in Hillscheid, Germany, under greenhouse conditions which approximate those generally used in commercial practice.

BRIEF DESCRIPTION OF THE INVENTION

The following traits have been repeatedly observed and are determined to be basic characteristics of 'Fisrobrav' in combination distinguish this geranium as a new and distinct cultivar:

1. Round, semi-double, bluish-pink flowers with bright red and white markings (eyes);

2. Wide inflorescences on strong peduncles, well above the foliage;

3. Large, medium green leaves with weak zonation;

4. Moderately vigorous growth, and medium to tall, somewhat open plant habit; and 5. Medium (mid season) spring flowering response.

Of the many commercial cultivars known to the present inventor, the most similar in comparison to 'Fisrobrav' are the parental varieties 'Fisbravo', and 'Valentine', and the commercial cultivar 'Americana Deep Rose' (U.S. Plant Pat. No. 9,383).

In comparison to 'Fisbravo', 'Fisrobrav' has medium green foliage, in contrast to the dark-green leaves of 'Fisbravo', larger leaves and a taller plant habit.

In comparison to 'Valentine', 'Fisrobrav' has a similar ground color of flowers, with added distinct red eyes, both on upper and lower petals, which 'Valentine' lacks. Furthermore, 'Fisrobrav' has larger leaves and medium-green foliage color, while 'Valentine' has relatively small, round, and dark-green leaves. In addition, 'Fisrobrav' grows more vigorously and develops a taller plant habit.

In comparision to 'Americana Deep Rose', 'Fisrobrav' has a somewhat lighter or less bluish general flower color, RHS 68 A, versus the flower color, RHS 72 C, of 'Americana Deep Rose', and with rose-red to cherry-red eyes, while 'Americana Deep Red' has somewhat deeper, bluish-red markings. Furthermore, 'Fisrobrav' has light green pedicels and more distinct zonation on leaves, while 'Americana Deep Rose' has light red pedicels and no or only very weak zonation. Both varieties grow vigorously, with 'American Deep Rose' developing an even wider plant habit.

BRIEF DESCRIPTION OF THE DRAWING

The accompanying photographic drawing shows typical flower and foliage characteristics of 'Fisrobrav' with colors being as true as possible with an illustration of this type. The drawing shows a flowering pot plant in a 14 cm container.

DETAILED BOTANICAL DESCRIPTION

In the following description color references are made to The Royal Horticultural Society Color Chart. The color values were determined indoors from plants developed in a green-house in May 2001 in Hillscheid, Germany. The measurements were taken in Hillscheid, Germany, in mid May, 2001, 10 weeks after planting of rooted cuttings.

Inflorescence:
- *Type.*—Umbel.
- *Shape.*—Wide, intermediate between semi-spherical and umbrella-shape.
- *Average diameter.*—99 mm.
- *Average depth.*—60 mm.
- *Peduncle length.*—138 mm.
- *Peduncle color.*—Green, RHS 143 B.
- *Pedicel length.*—33.6 mm.
- *Pedicel color.*—Light green, RHS 144 B, no anthocyanin.
- *Number of flowers per umbel.*—About 30.

Corolla:
- *Average diameter.*—52 mm.
- *Form.*—Semi-double.
- *Shape.*—Round, flat to slightly cup-shaped.
- *Number of petals.*—8.5.
- *Number of petaloids.*—0–2, narrow, color RHS 68 A (Both surfaces).
- *Shape of petals.*—Obovate, base attenuate, upper end is rounded, margin is entire.
- *Size of petals.*—Upper petals 26–28 mm long, 19–22 mm wide; lower petals 24–25 mm long, 24–26 mm wide.
- *Color (general tonality from a distance of three meters)*.—Bluish pink.
- *Color of upper petals.*—Main part RHS 68 A with RHS 155 A base.
- *Markings of upper petals.*—Rose-red eyes, RHS 57 C, diameter 6–7 mm.
- *Color of lower petals.*—RHS 68 A.
- *Markings of lower petals.*—Cherry-red eyes, RHS 57 B, diameter 4–5 mm.
- *Color of lower surface of petals.*—Mainly RHS 68 B, most intense near margin, almost white at the middle and lower part of petal RHS 75 D.
- *Color of sepals.*—Outer surface light green, RHS 144 B; inner surface light green, RHS 144 B.
- *Number of sepals.*—5.
- *Shape of sepals.*—Linear to lanceolate, acute tip, truncate base, surface with weak, very short pubescence, margin entire.
- *Size of sepals.*—11 mm long, 4 mm wide for the largest upper sepal, 2–3 mm in width for the other sepals.

Bud (just before petals unfold):
- *Shape.*—Elliptical.
- *Color (sepals).*—Light green, RHS 144 A.
- *Color (petals).*—Pink, RHS 68 A, near margin, to very light pink, RHS 73 D.
- *Length.*—19–20 mm.
- *Width.*—9–10 mm.

Reproductive organs:
- *Androecium.*—7 fertile anthers, filaments white, RHS 155 D, to light pink, RHS 68 B, moderate pollen, orange, RHS 33 A.
- *Gynoecium.*—One pistil, style and stigma deep pink, RHS 57 C, 5 to 6 lobed stigma.
- *Fertility/seed set.*—Occasionally a few seeds are developed. Fruit: Oblong, about 6 mm in diameter, with rostrum (beak), total length 40–42 mm. Seed: Oblong, 4–5 mm long, brown, RHS 177 B.

Spring flowering response period: In Hillscheid, Germany, in 2000 plants had on average 1.0 flowers opened 8 weeks after planting of rooted cuttings.

Outdoor flower production: Continuously flowering, the flower count in 2000 in Hillscheid, Germany, indicated about 2.3 inflorescences per plant in mid May.

Durability: Good stability of flower color, good heat tolerance relatively good rain resistance.

Lastingness of the individual flower: About 18 days at 18° C., about 18 days for the umbel.

Pest/disease resistance/susceptibility: No observations to date.

Fragrance: None.

PLANT

Foliage:
- *Shape.*—Kidney-shaped, cordate, open base, with weak lobes.
- *Margin.*—Bicrenated.
- *Texture.*—Upper surface smooth, velvety.
- *Size of leaf.*—97.5 mm wide, 73 mm. long.
- *Color of upper surface.*—Medium green, approximately RHS 137 D.
- *Color of zonation.*—Brown, about RHS 166 A.
- *Color of lower surface.*—Between RHS 137 D to 144 A.
- *Petioles.*—50–65 mm long, 2–3 mm diameter, light green in color, approximately RHS 143 C.

General appearance and form:
- *Stem color.*—Light green, RHS 143 B to 143 C.
- *Internode length.*—5–15 mm.
- *Branching pattern.*—3.8 branches on average.
- *Size of plants.*—Height 15.3 cm, width 29.3 cm, as measured from the base of the main stem to the surface of the foliage canopy without the inflorescences.

I claim:

1. A new and distinct cultivar of geranium plant named 'Fisrobrav', as described and illustrated herein.

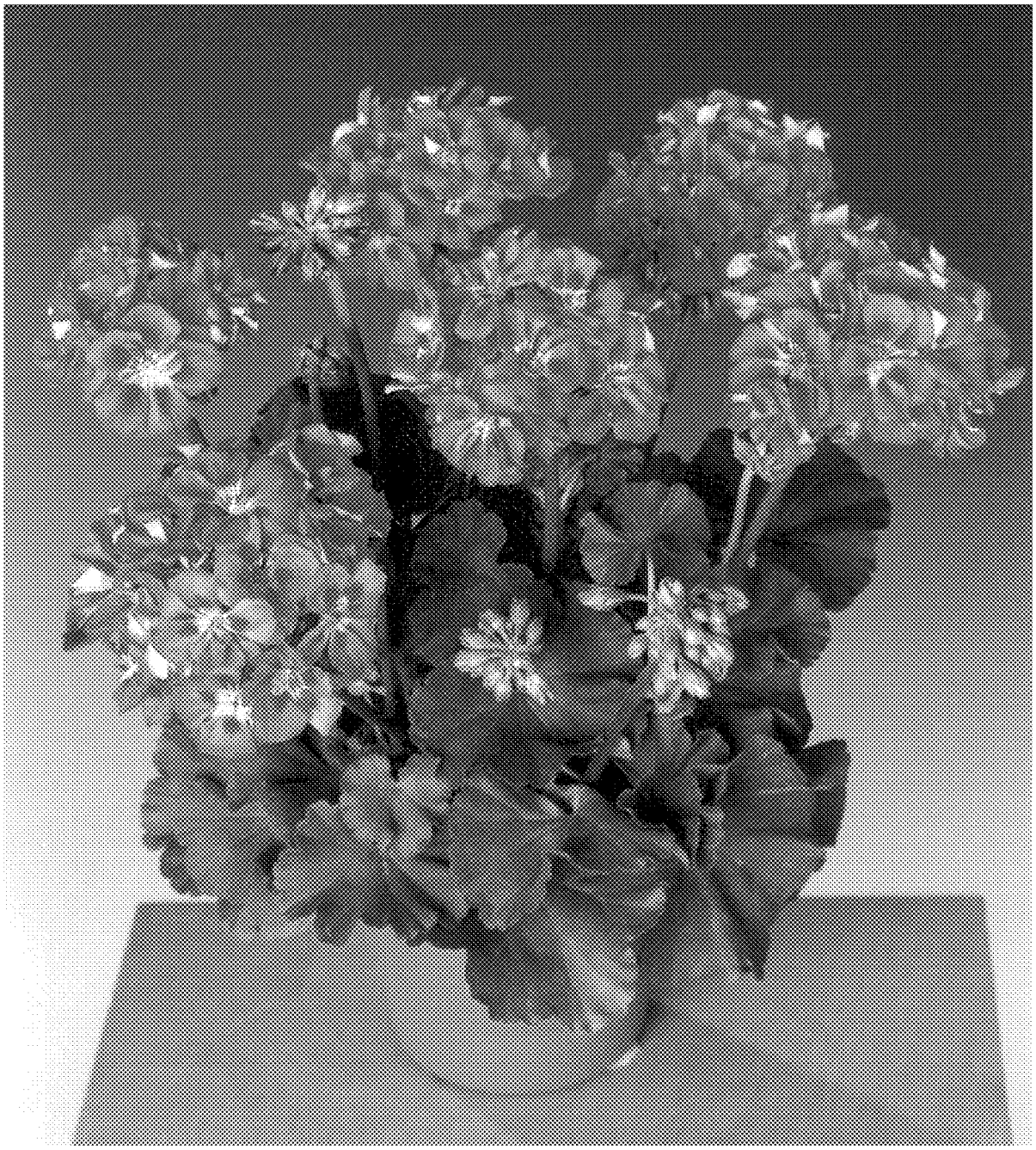

* * * * *